United States Patent [19]

Norton

[11] 3,965,160

[45] June 22, 1976

[54] REMOVAL OF IRON IMPURITIES FROM AROMATIC CARBOXYLIC ACIDS

[75] Inventor: Richard V. Norton, Wilmington, Del.

[73] Assignee: Sun Ventures, Inc., Philadelphia, Pa.

[22] Filed: Apr. 3, 1974

[21] Appl. No.: 457,666

[52] U.S. Cl.................... 260/515 P; 260/515 R; 260/525
[51] Int. Cl.$^2$........................................ C07C 51/42
[58] Field of Search............ 260/515 P, 515 R, 525

[56] References Cited
UNITED STATES PATENTS

| | | | |
|---|---|---|---|
| 3,243,456 | 3/1966 | Caldwell et al. | 260/525 |
| 3,833,677 | 9/1974 | Gelbein et al. | 260/515 |

OTHER PUBLICATIONS

Hajek et al. Coll. Czech. Chem. Commun., vol. 36 (1971) pp. 84–91.
Sherif Ind. Eng. Chem. Prod. Res. Devel. vol. 9, no. 3 (1970) pp. 408–412.

*Primary Examiner*—James A. Patten
*Attorney, Agent, or Firm*—J. Edward Hess; Donald R. Johnson; Paul Lipsitz

[57] ABSTRACT

A process for removing iron contamination of aromatic carboxylic acids by oxidizing an aqueous solution of the ammonium salt of the acid to form insoluble iron compounds, separating the insoluble compounds, and converting the acid salt to free acid.

7 Claims, No Drawings

REMOVAL OF IRON IMPURITIES FROM AROMATIC CARBOXYLIC ACIDS

In the manufacture of aromatic acids the acid products are frequently contaminated by iron derived from solubilization of iron or steel equipment used in the manufacturing process. Such contamination discolors the acid products and also may interfere with subsequent use of such acids. This is particularly true in the case of those aromatic acids used in the manufacture of polymeric materials; e.g., polyesters made from terephthalic, isophthalic, 2,6-naphthalene dicarboxylic acid and the like. The acid intermediates used for polyester formation must be color-free and of high purity and thus any such contamination must be removed.

It is known in the art that iron salts of aromatic acids are colored crystalline hydrates and in an article by F. G. Sherif (Ind-Eng. Chem. Prod. Res. Develop, Vol. 9, No. 3, 1970) it is pointed out with reference to iron terephthalate, that on prolonged boiling in water the iron hydrate is hydrolyzed to insoluble basic salts—e.g., Fe $(OH)C_6H_4(COO)_2$. Also disclosed is that on prolonged treatment with water at 270°C the iron basic salt is completely hydrolyzed to the hydrated iron oxide and free terephthalic acid (TPA). This article further points out that in the air oxidation of p-xylene in acetic acid to form terephthalic acid iron is believed to be leached out of the stainless steel reactors as ferrous iron by acetic acid and TPA at the temperature of the reaction, 130° to 150°C. It is then air-oxidized immediately to the ferric state, most likely to an acetic acid-soluble form. If washing is incomplete and if water or a water-acetic acid mixture is used for washing at high temperature, the soluble iron incorporated in the TPA particles hydrolyzes to the less soluble basic iron acetate and iron terephthalate. If TPA is then recrystallized from water (at 160° to 270°C), the iron hydrolyzes further to the hydrated ferric oxide. Once iron oxide is formed, it is difficult to remove, even by retreatment with acetic acid.

A new technique has now been discovered to remove iron contamination from TPA and other aromatic carboxylic acids and this novel process is particularly valuable with aromatic acids obtained through ammoxidation of alkyl-substituted aromatic hydrocarbons where the nitrile product is hydrolyzed to obtain the acid.

In accord with the invention a process is provided for removing iron contamination of aromatic carboxylic acids which comprises oxidizing an aqueous solution of the ammonium salt of the aromatic acid, preferably the hydrolysis solutions from aromatic nitriles, to form insoluble iron compounds, separating the insoluble compounds, and converting the acid salt to free acid.

The aromatic acids with which the process of the invention is useful will comprise a wide variety of such acids, preferably those of the benzene and naphthalene series. Most preferably, the acids used in the process will be benzoic acid and the dicarboxylic acids employed as polyester intermediates; e.g., phthalic acid, terephthalic acid, isophthalic acid, 2,6- naphthalene dicarboxylic acid, 1,5-naphthalene dicarboxylic acids and the like. As indicated the process is particularly useful with those acids made by aqueous hydrolysis of the nitriles obtained by ammoxidation of the appropriate aromatic hydrocarbon since upon hydrolysis of the nitrile, the ammonium salt of the acid is formed in-situ and thus the aqueous solution of the hydrolysis products is immediately ready for the purification process of the invention. Thus, for example ammoxidation of xylenes yields isophthalonitrile and terephthalonitrile and ammoxidation of the appropriate isomers of the dimethylnaphthalenes yield compounds such as 2,6-dicyanonaphthalene, 1,5-dicyanonaphthalene, and the like. Of course, an iron-contaminated free acid may be used in the process simply by the addition of ammonium hydroxide in an amount sufficient to form the acid salt. In the case of a dicarboxylic acid, the disalt should preferably be formed, although the presence of some mono salt is not objectionable as long as the system is a homogeneous solution and not a slurry at the operating temperature.

The oxidation may be made to occur with the normally dissolved oxygen in the aqueous solution, but since this will require a rather long time to effect complete oxidation of the iron present it is not a preferred method. Preferably, air or other oxygen source will be used to treat the acid salt solution and most preferably this will be done at an elevated temperature; e.g., from about 80°to about 250°C. This is readily accomplished simply by passing air through the refluxing aqueous solution or by using a pressure vessel containing air or oxygen. As the iron present is converted to an insoluble form its presence becomes obvious from the appearance of a reddish brown particulate or collodial material. At the same time, the liquid becomes clearer and when filtered the filtrate is colorless rather than the brownish or pale yellow color of the contaminated material. When oxidation has been carried out sufficiently long to convert all of the iron to an insoluble form, as evidenced by a clear colorless filtrate, the solution is separated from the precipitated solid. Normally the time required for the oxidation will range from about 0.5 to about 12 hours and will, of course, vary with temperature, degree of contamination, amount of oxygen used and the like. The clear, colorless filtrate is then treated at room temperature with an acid, preferably hydrochloric or acetic acid, to convert the salt to free acid which precipitates out due to its low water solubility and the free acid is filtered off, washed if desired and taken for any intended use. As an alternative to converting the ammonium salt of the aromatic acid to free acid by an acid precipitation technique, the aqueous solution of the ammonium salt may be heated to drive off ammonia, thus converting the salts directly to the solid free acid or to its monoammonium salt dispersed in the aqueous medium from which it is readily separated.

In order to further illustrate the invention the following examples are given.

EXAMPLE I

Terephthalic acid is prepared by distillation under pressure at 250°C. of ammonia and water from a terephthalonitrile hydrolyzate solution prepared in stainless steel equipment. The terephthalic acid (TPA) contains: 0.69% N, 4.7ppm Fe, 0.2ppm Cr, 0.3ppm Cu, and 2.3ppm Ti.

Acidification of one portion of the filtrate remaining after separation of the TPA yields terephthalic acid containing 10.9ppm Fe. A second portion of the filtrate is set aside for one month during which time the formation of a reddish colloidal sludge is observed. The sludge suspension is filtered through a "filter-cel" mat yielding a clear colorless solution. Evaporation of a portion of the filtrate, followed by pyrolysis of the ammonium salts at 250°C in $N_2$ yields colorless terephthalic acid containing less than 0.1ppm combined of Fe, Cr, Ni and Cu.

EXAMPLE II

Crude terephthalic acid is prepared by venting ammonia (1.684 moles) at 250°C from a terephthalonitrile (1 mole) hydrolyzate solution. Analysis is 0.16% N; 0.2ppm Ni, 0.2ppm Cu, 2.4ppm Fe, and 0.1ppm Cr.

A portion of the filtrate remaining after separation of the TPA is evaporated yielding a mixture of TPA, ammonia salts and amides containing 18.1ppm Fe. The remaining filtrate (tan solution) is refluxed overnight while bubbling air through the solution. The next day a tan deposit is noted on the inside of the flask and the solution appears to be less intensely colored. Refluxing and aireation is continued for another day. A definite coating of reddish-brown material is observed to have formed on the flask and the solution was noticeably lighter in color. The solution was filtered through "filter-cel" yielding a clear colorless solution.

Acidification of the filtrate with HCl gave terephthalic acid containing less than 0.1ppm total of Fe, Cr, Cu and Ni.

EXAMPLE III

Naphthalene-2,6-dinitrile is hydrolyzed in stainless steel equipment yielding a tan solution which upon acidification of a portion gives 2,6-naphthalene dicarboxylic acid containing more than 250ppm of iron and other metals. Aliquots of 100 ml each of the original hydrolyzate are oxidized and after filtration, the filtrate is acidified yielding the 2,6-diacid. The conditions of oxidation and purity of acid obtained is shown in the following table.

| Example | Time | Oxidation Temp. | $O_2$ supply | Total Iron in 2,6-diacid |
|---|---|---|---|---|
| A | 3 hrs. | 100°C | air | 233 |
| B | 24 hrs. | 100°C | air | 100 |
| C | 48 hrs. | 100°C | air | 75 |
| D | 12 hrs. | 200°C | sealed bomb | 75 |
| E | 24 hrs. | 200°C | sealed bomb | 50 |

EXAMPLE IV

An acidified solution of the diammonium salt of TPA (obtained by aqueous hydrolysis of terephthalonitrile) containing 175ppm iron in the TPA is oxidized at 200°C. for 12 hours in a sealed Paar bomb under air pressure at 500 psi.

The resulting tan solution is filtered and the clear, colorless solution spray pyrolyzed to yield the monoammonium salt of TPA (MAT) by the process of U.S. Pat. No. 3,770,819 yielding MAT containing less than 50 but more than 40 ppm Fe. Acidification of the MAT gives TPA containing between 40 and 50 ppm of iron.

The invention claimed is:

1. A process for removing iron contamination of aromatic carboxylic acids of the benzene and naphthalene series obtained by aqueous hydrolysis of the corresponding nitriles which comprises oxidizing said aqueous nitrile hydrolysis products comprising ammonium salts of said aromatic carboxylic acids with air at a temperature between about 80° and about 250°C. to form insoluble iron compounds, separating said insoluble compounds and converting the acid ammonium salts to free acid.

2. The process of claim 1 where the nitrile is derived from a xylene.

3. The process of claim 2 where the nitrile is derived from a dimethylnaphthalene.

4. The process of claim 1 where the aromatic acid is terephthalic acid.

5. The process of claim 1 where the aromatic acid is isophthalic acid.

6. The process of claim 1 where the aromatic acid is 2,6-naphthalene dicarboxylic acid.

7. A process for removing iron contamination from the diammonium salt of terephthalic acid obtained by aqueous hydrolysis of terephthalonitrile which comprises oxidizing said aqueous nitrile hydrolysis products with air at a temperature between about 80° and about 250°C. to form insoluble iron compounds, separating said insoluble compounds and converting the purified diammonium salt to purified monoammonium salt by pyrolysis of said diammonium salt.

* * * * *